US012379266B2

(12) United States Patent
Lenzi et al.

(10) Patent No.: US 12,379,266 B2
(45) Date of Patent: Aug. 5, 2025

(54) FORCE AND TORQUE SENSOR FOR PROSTHETIC AND ORTHOPEDIC DEVICES

(71) Applicant: University of Utah Research Foundation, Salt Lake City, UT (US)

(72) Inventors: Tommaso Lenzi, Salt Lake City, UT (US); Lukas Gabert, Murray, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 909 days.

(21) Appl. No.: 17/268,349

(22) PCT Filed: Aug. 21, 2019

(86) PCT No.: PCT/US2019/047536
§ 371 (c)(1),
(2) Date: Feb. 12, 2021

(87) PCT Pub. No.: WO2020/041491
PCT Pub. Date: Feb. 27, 2020

(65) Prior Publication Data
US 2021/0247249 A1    Aug. 12, 2021

Related U.S. Application Data

(60) Provisional application No. 62/721,399, filed on Aug. 22, 2018.

(51) Int. Cl.
*A61F 2/68*    (2006.01)
*A61F 2/64*    (2006.01)
(Continued)

(52) U.S. Cl.
CPC ............... *G01L 1/122* (2013.01); *A61F 2/68* (2013.01); *G01D 5/145* (2013.01); *A61F 2/64* (2013.01);
(Continued)

(58) Field of Classification Search
CPC .... A61F 2002/6863; A61F 2/68; G01L 1/122; G01D 5/145
See application file for complete search history.

(56) References Cited

U.S. PATENT DOCUMENTS 4,407,496 A    10/1983    Johnson
4,483,194 A    11/1984    Rudolf
(Continued)

FOREIGN PATENT DOCUMENTS

CN    101336849 A    1/2009
CN    102204918 A    10/2011
(Continued)

OTHER PUBLICATIONS

Beil, Jonas, and Tamim Asfour. "New mechanism for a 3 DOF exoskeleton hip joint with five revolute and two prismatic joints." 2016 6th IEEE International Conference on Biomedical Robotics and Biomechatronics (BioRob). IEEE, 2016.
(Continued)

*Primary Examiner* — Christopher D. Prone
(74) *Attorney, Agent, or Firm* — Workman Nydegger

(57) ABSTRACT

The present disclosure describes sensor devices that can be readily integrated with prosthetic devices to provide sensing of force and torque applied to the prosthetic device during use. The sensor device includes an adaptor section that readily connects to standard prosthetic components and a base section. The base section has a deflectable portion and a fixed portion. Cantilevers in the deflectable portion house magnets and corresponding Hall effect sensors are housed in the fixed portion. When axial and/or torsional forces are applied, the cantilevers deflect relative to the fixed section and the Hall effect sensors provide a corresponding output that correlates to the axial and/or torsional forces applied.

20 Claims, 4 Drawing Sheets

(51) Int. Cl.
*A61F 2/66* (2006.01)
*G01D 5/14* (2006.01)
*G01L 1/12* (2006.01)

(52) U.S. Cl.
CPC ..... *A61F 2/6607* (2013.01); *A61F 2002/6863* (2013.01)

(56) References Cited

U.S. PATENT DOCUMENTS

| | | | |
|---|---|---|---|
| 4,762,006 | A | 8/1988 | Asakawa et al. |
| 4,772,928 | A | 9/1988 | Dietrich et al. |
| 5,027,657 | A | 7/1991 | Juckenack et al. |
| 5,998,742 | A | 12/1999 | Liu et al. |
| 6,166,013 | A | 12/2000 | Coghlan et al. |
| 6,237,399 | B1 | 5/2001 | Shivaram et al. |
| 6,829,510 | B2 | 12/2004 | Nathan et al. |
| 7,279,010 | B2 | 10/2007 | Cheng |
| 7,347,954 | B2 | 10/2008 | Sakano |
| 7,437,954 | B2 | 10/2008 | Sakano |
| 7,485,152 | B2 | 2/2009 | Haynes et al. |
| 8,087,498 | B2 | 1/2012 | Dupuis et al. |
| 8,500,823 | B2 | 8/2013 | Herr et al. |
| 8,696,764 | B2 | 4/2014 | Hansen et al. |
| 8,800,366 | B2 | 8/2014 | Scott et al. |
| 8,870,967 | B2 | 10/2014 | Herr et al. |
| 8,974,543 | B2 | 3/2015 | Balboni et al. |
| 9,089,443 | B2 | 7/2015 | Nakaya et al. |
| 9,101,451 | B2 | 8/2015 | Chugunov |
| 9,717,606 | B2 | 8/2017 | Gramnaes |
| 9,770,347 | B2 | 9/2017 | Shen |
| 9,808,357 | B2 | 11/2017 | Langlois |
| 10,335,291 | B2 | 7/2019 | Djian et al. |
| 10,342,681 | B2 | 7/2019 | Herr et al. |
| 12,048,668 | B2 | 7/2024 | Sarkisian et al. |
| 2002/0147336 | A1 | 10/2002 | Liu et al. |
| 2003/0104365 | A1 | 6/2003 | Gurney et al. |
| 2004/0121407 | A1 | 6/2004 | DiStefano et al. |
| 2005/0080061 | A1 | 4/2005 | Belanoff |
| 2007/0225620 | A1 | 9/2007 | Carignan et al. |
| 2008/0287834 | A1* | 11/2008 | Pusch .................. A61F 2/76 600/595 |
| 2009/0088425 | A1 | 4/2009 | Bailly et al. |
| 2009/0229378 | A1 | 9/2009 | Kurtz et al. |
| 2010/0169988 | A1 | 7/2010 | Kohli et al. |
| 2012/0028358 | A1 | 2/2012 | Solodushko et al. |
| 2013/0237883 | A1 | 9/2013 | Malosio et al. |
| 2013/0319135 | A1* | 12/2013 | Okada .................. G01L 1/2206 73/862.043 |
| 2014/0276261 | A1 | 9/2014 | Caires et al. |
| 2015/0105782 | A1* | 4/2015 | D'Lima ............. A61F 2/4657 606/90 |
| 2015/0321341 | A1 | 11/2015 | Smith |
| 2016/0041149 | A1 | 2/2016 | Lindquist et al. |
| 2016/0158029 | A1 | 6/2016 | Kuiken et al. |
| 2016/0242936 | A1 | 8/2016 | Goldfarb et al. |
| 2016/0296346 | A1 | 10/2016 | Burke et al. |
| 2016/0331560 | A1 | 11/2016 | Tong et al. |
| 2017/0128312 | A1 | 5/2017 | Park et al. |
| 2018/0116828 | A1 | 5/2018 | Quinn et al. |
| 2018/0147073 | A1 | 5/2018 | Ly et al. |
| 2018/0194000 | A1* | 7/2018 | Smith .................... B25J 9/0006 |
| 2018/0256372 | A1 | 9/2018 | Boiten et al. |
| 2018/0325766 | A1 | 11/2018 | Arzanpour et al. |
| 2018/0327373 | A1 | 11/2018 | Yang et al. |
| 2019/0020934 | A1 | 1/2019 | Goyal et al. |
| 2019/0060154 | A1 | 2/2019 | Lee et al. |
| 2019/0111299 | A1 | 4/2019 | Radcliffe et al. |
| 2019/0160653 | A1 | 5/2019 | Lee et al. |
| 2019/0209348 | A1* | 7/2019 | Casler, Jr. ............ A61H 1/0266 |
| 2019/0314978 | A1 | 10/2019 | Hunt et al. |
| 2020/0038279 | A1 | 2/2020 | Saccares et al. |
| 2021/0053208 | A1 | 2/2021 | Paine et al. |
| 2021/0161748 | A1 | 6/2021 | Kim et al. |
| 2021/0244599 | A1 | 8/2021 | Arzanpour et al. |
| 2021/0338458 | A1 | 11/2021 | Lenzi et al. |
| 2021/0369533 | A1 | 12/2021 | Huang et al. |
| 2022/0401284 | A1 | 12/2022 | Arzanpour et al. |
| 2023/0007984 | A1 | 1/2023 | Sarkisian et al. |
| 2024/0325230 | A1 | 10/2024 | Sarkisian et al. |

FOREIGN PATENT DOCUMENTS

| | | |
|---|---|---|
| CN | 103271783 A | 9/2013 |
| CN | 108836583 A | 11/2018 |
| CN | 109044742 A | 12/2018 |
| CN | 209695751 U | 11/2019 |
| CN | 111110520 A | 5/2020 |
| DE | 4016147 A1 | 11/1991 |
| EP | 0795741 A2 | 9/1997 |
| EP | 1933775 A2 | 6/2008 |
| EP | 2178680 A2 | 4/2010 |
| GB | 2302949 A | 2/1997 |
| JP | 2012-125279 A | 7/2012 |
| JP | 2015-212010 A | 11/2015 |
| JP | 2020-531066 A | 11/2020 |
| KR | 10-2017-0111255 A | 10/2017 |
| WO | 2007/027668 A2 | 3/2007 |
| WO | 2009/015751 A1 | 2/2009 |
| WO | 2009/016478 A2 | 2/2009 |
| WO | 2016/094413 A1 | 6/2016 |
| WO | 2017/059115 A1 | 4/2017 |
| WO | 2018/087997 A1 | 5/2018 |
| WO | 2019/198269 A1 | 10/2019 |
| WO | 2019/218056 A1 | 11/2019 |

OTHER PUBLICATIONS

Beil, Jonas, Charlotte Marquardt, and Tamim Asfour. "Self-aligning exoskeleton hip joint: kinematic design with five revolute, three prismatic and one ball joint." 2017 International Conference on Rehabilitation Robotics (ICORR). IEEE, 2017.

International Search Report and Written Opinion dated Nov. 14, 2019 for PCT/US2019/048489.

International Search Report and Written Opinion received for PCT Patent Application No. PCT/US19/48489, mailed on Nov. 14, 2019, 8 ages.

International Search Report and Written Opinion received for PCT Patent Application No. PCT/US2020/000009, mailed on Feb. 9, 2021, 16 pages.

Leisle et al., "Cellular encoding of Cy dyes for single-molecule imaging", Elite vol. 5, 2016, pp. e19088.

Liu et al., "Imaging Live-Cell Dynamics and Structure at the Single-Molecule Level", Mol. Cell., vol. 58 No. 4, 2015, pp. 644-659.

Peng et al., "Site-specific bioorthogonal labeling for fluorescence imaging of intracellular proteins in living cells", J. Am. Chem. Soc., vol. 138, No. 43, 216, pp. 14423-14433.

Syed et al., "Expanding the Zebrafish Genetic Code through Site-Specific Introduction of Azido lysine", Bicyclononyne-lysine, and Diazirine-lysine. Int. J. Mol. Sci., vol. 20, No. 10, May 2019, pp. 2577.

Written Opinion received for PCT Patent Application No. PCT/US2020/000009, mailed on Jul. 22, 2020, 6 pages.

International Search Report and Written Opinion received for PCT Patent Application No. PCT/US21/23231, mailed on Jun. 14, 2021, 7 pages.

Lenzi et al., "Actively variable transmission for robotic knee prostheses", 2017 IEEE International Conference on Robotics and Automation (ICRA), IEEE, May 29, 2017 (May 29, 2017), pp. 6665-6671.

International Search Report and Written Opinion dated Nov. 20, 2019 for PCT/US2019/047536.

Supplementary European Search Report received for EP Patent Application No. 21770510.2, mailed on Feb. 6, 2024, 11 pages.

* cited by examiner

FORCE AND TORQUE SENSOR FOR PROSTHETIC AND ORTHOPEDIC DEVICES

CROSS-REFERENCE TO RELATED APPLICATIONS

This application claims priority to PCT Application No. PCT/US2019/047536, filed Aug. 21, 2019 and titled "FORCE AND TORQUE SENSOR FOR PROSTHETIC AND ORTHOPEDIC DEVICES", which application claims priority to and the benefit of U.S. Provisional Patent Application Ser. No. 62/721,399, filed Aug. 22, 2018 and titled "FORCE AND TORQUE SENSOR FOR PROSTHETIC AND ORTHOPEDIC DEVICES". Each of the aforementioned applications are incorporated herein by this reference in their entirety.

BACKGROUND

The loss of a limb can have an adverse impact on the person losing the limb. Lower limb amputations, in particular, can adversely affect the ability to walk. Amputations such as lower limb amputations are also becoming more common as a result of negative health trends, including increases in cardiovascular disease and complications related to diabetes. There is accordingly a long felt and ongoing need for suitable prostheses for amputees.

A suitable prosthesis should be tailored to the individual amputee's needs. With a lower limb prosthesis, for example, an individual's specific movement profile (i.e., gait and related movement patterns) can have a profound effect on the functionality of the prosthetic device. In particular, the individual amputee's specific movement profile will produce corresponding torque and force stresses in the prosthetic device, and these may differ from person to person based on different movement profiles, different particular type of amputation, and a variety of other anatomical and/or device factors. Properly configuring and making fine adjustments to the device therefore depends on an accurate determination of the forces and torques applied to the prosthetic device during use. Excessive pressure and shear resulting from misalignment and/or improper configuring of the prosthesis can cause pain and discomfort in the user.

Currently available methods for sensing force and torque include specialized and heavily instrumented treadmills or walkways used in combination with motion capture camera systems. This type of instrumentation is expensive and has limited practical application due to the need for a full laboratory setting. Some sensors have been developed for integration with the prosthesis. These sensors conventionally make use of multiple load cells, usually based on strain gauges, to make the force/torque measurements. However, current sensors such as these are relatively expensive and tend to take up a lot of space on the prosthesis. The expense and the large form factor can reduce the number of potential users who can use the corresponding prosthesis.

Accordingly, there is a long felt and ongoing need for sensor devices that may be readily integrated with a prosthetic device and that provide robust force and torque sensing during use of the prosthetic device.

BRIEF SUMMARY

The present disclosure is directed to sensor devices configured to measure applied force and torque. Sensor devices may be integrated with prosthetic devices to provide sensing of force (e.g., axial force) and torque applied to the prosthetic device during use. In one embodiment, a sensor device includes a base section having a fixed portion and a deflectable portion. The deflectable portion includes an inner point and one or more cantilevers extending outward in a coplanar fashion from the inner point. The fixed portion is spaced apart from the deflectable portion such that the one or more cantilevers of the deflectable portion are deflectable relative to the fixed portion. A pillar extends between the inner point of the deflectable portion and the fixed portion to mechanically couple the deflectable portion to the fixed portion.

The sensing device also includes a plurality of sensing components configured to measure deflection of the deflectable portion relative to the fixed portion. The sensing components may include Hall sensors and magnets, resistive potentiometers, capacitive displacement sensors, optical sensors, or combinations thereof. In a preferred embodiment, the sensing device includes at least one magnet and at least one corresponding Hall effect sensor together configured to measure magnetic field strength resulting from a distance between the Hall effect sensor and the corresponding magnet. In such an embodiment, the sensing components are arranged such that output from the at least one Hall effect sensor relates to deflection of the one or more cantilevers relative to the fixed portion. For example, the magnet may be attached at an outer edge of a corresponding cantilever, and the Hall effect sensor may be attached on the fixed portion of the base section, or vice versa.

In some embodiments, a sensing device may also include an adaptor section having a bottom surface and a connection element extending away from the bottom surface, wherein at least outer edges of the one or more cantilevers are in mechanical contact with the bottom surface of the adaptor section. The connection element may be, for example, a male pyramid adaptor.

Additional features and advantages will be set forth in part in the description that follows, and in part will be obvious from the description, or may be learned by practice of the embodiments disclosed herein. The objects and advantages of the embodiments disclosed herein will be realized and attained by means of the elements and combinations particularly pointed out in the appended claims. It is to be understood that both the foregoing brief summary and the following detailed description are exemplary and explanatory only and are not restrictive of the embodiments disclosed herein or as claimed.

BRIEF DESCRIPTION OF THE DRAWINGS

A more particular description will be rendered by the embodiments illustrated in the appended drawings. It is appreciated that these drawings depict only exemplary embodiments of the disclosure and are therefore not to be considered limiting of its scope. In the accompanying drawings.

DETAILED DESCRIPTION

The present disclosure describes sensor devices capable of being integrated with a prosthetic and/or orthopedic device to provide sensing axial and/or torsional forces applied to the prosthetic device during use. The sensor devices described herein beneficially provide robust sensing while also having a compact design that allows for ready integration with standard prosthetic devices. As explained in more detail below, the sensor devices described herein make use of magnetic field sensors to measure displacement related to force and/or torque applied to the prosthetic device. Other sensor systems for measuring displacement may additionally or alternatively be used. For example, a sensor device may utilize one or more of resistive potentiometers, capacitive displacement sensors, and optical sensors to measure displacement related to force and/or torque applied to the prosthetic device.

Figure 1:
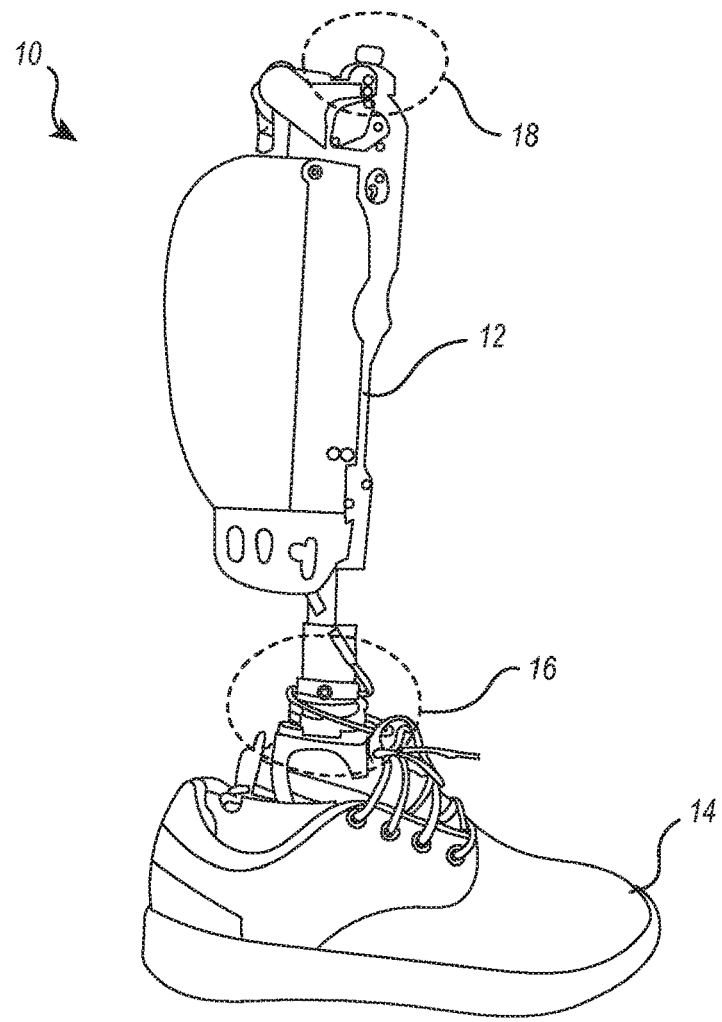
FIG. 1 illustrates an exemplary lower limb prosthesis, showing common regions where a standard pyramid adaptor may be utilized to connect the prosthesis to other prosthetic components.

FIG. 1 illustrates an exemplary lower limb prosthetic device 10 that includes a pylon section 12 and a foot section 14. Prosthetic devices such as the one shown often include standard fittings at the ankle section 16 and the knee section 18. For example, the fitting at the ankle section 16 can be used to attach different foot components, and the fitting at the knee section 18 can be used to attach the prosthetic device 10 to the socket (typically worn on the user's residual limb) or to an upper pylon portion that then attaches to the socket. Other prosthetic devices may be configured differently. For example, a prosthetic device designed for a below-the-knee transtibial amputee will not include a prosthetic knee joint. As used herein, the term "prosthetic component" refers to any prosthesis section that is directly or indirectly attachable to another prosthesis section, such as a foot component, pylon, powered or passive joint component, or socket.

The illustrated prosthetic device 10 includes a sensor integrated at the ankle portion 16. However, other embodiments may additionally or alternatively include a sensor positioned at another location of a prosthesis, such as at the knee portion 18. The illustrated prosthetic device 10 has a powered knee and powered ankle. The sensor devices described herein are particularly useful in conjunction with prostheses having one or more powered joints such as shown, as the determined force and/or torque information can be utilized to make adjustments to the power and/or range of movement provided by the powered components of the prosthesis. However, it will be understood that the use of the described sensor devices need not be limited to such powered prostheses. Sensor devices may also, for example, be beneficially utilized in conjunction with prostheses having one or more joints configured for passive articulation.

Figure 2:
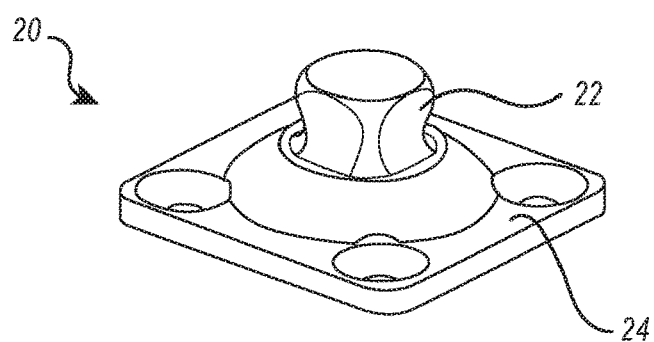
FIG. 2 illustrates a standard prosthetic pyramid adaptor.

A typical prosthetic device includes standard fittings at the ankle section 16 and knee section 18 (and in some cases at other sections such as where the device is intended to connect to the socket). One of the most common fittings is a pyramid adaptor 20 such as the one shown in FIG. 2. The pyramid adaptor 20 usually includes a pyramid section 22 connected to a base 24 with fastening holes or some other type of fastening component. FIG. 2 illustrates a standard 4-hole male pyramid adaptor. The exemplary sensor embodiments are shown herein have a similar male pyramid adaptor as a connection element. It will be understood, however, that the particular type of connection element utilized in a sensor is not limited to male pyramid adaptors. For example, other embodiments may have a connection element that includes one or more of a female pyramid coupler, a threaded component, a clamp, a magnetic coupler, other fasteners or adaptors, or combinations thereof.

Figure 3:
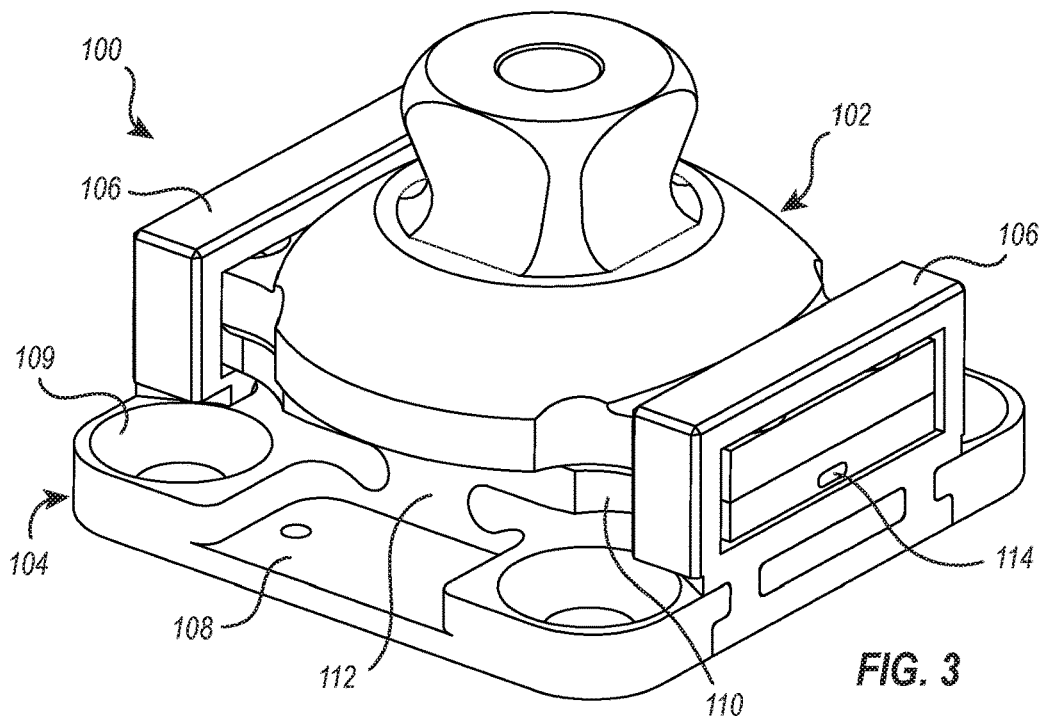
FIG. 3 illustrates an exemplary embodiment of a prosthetic sensor device configured for integration with a prosthetic device for detecting force and torque during use of the prosthetic device.
Figure 4:
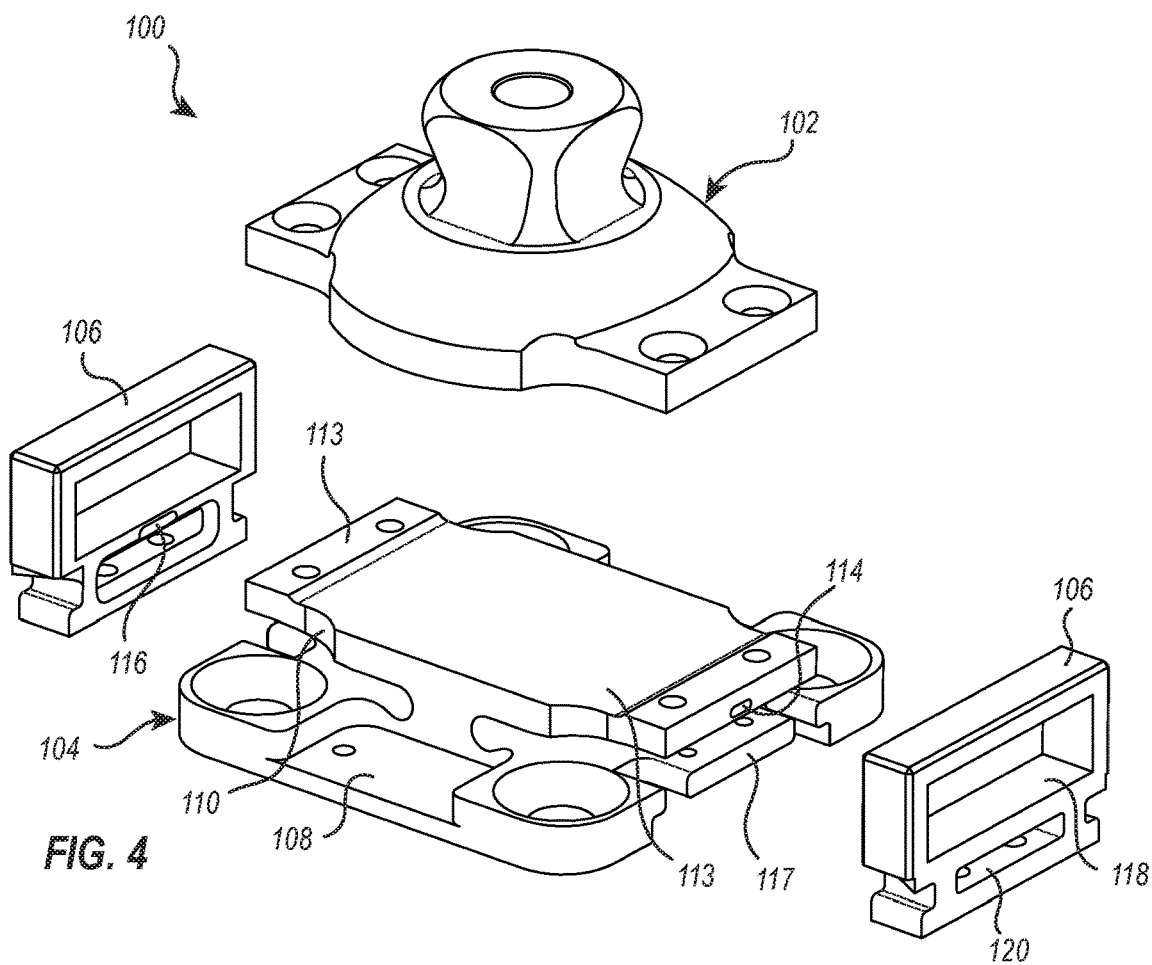
FIG. 4 is an exploded view of the sensor device of FIG. 3.

FIGS. 3 and 4 illustrate an exemplary embodiment of a prosthetic sensor device 100, with FIG. 3 showing the assembled device and FIG. 4 showing an exploded view of the device. The illustrated device 100 includes an adaptor section 102 and a base section 104. The adaptor section 102 is shown here as having a connection element in the form of a male pyramid but may be alternatively configured with a different type of connection element according to particular application needs or preferences.

The base section 104 includes a fixed portion 108 joined to a deflectable portion 110 by way of a pillar 112. The base section 104 may also include one or more fastening structures, such as fastening holes 109, for ease of attaching the sensor device to a prosthetic device at the desired location. In this embodiment, the deflectable portion 110 includes two cantilevers 113 attached to the pillar 112 (at a location that defines an "inner point") and extending outward from the pillar 112 in opposite directions. As explained in more detail below, other embodiments may include other numbers and/or orientations of cantilever components. Use of a pillar 112 and cantilevers 113 is beneficial in that it allows deflection of the cantilevers 113 in response to applied forces without requiring the entire bottom surface of the deflectable portion 110 to flex. That is, the pillar 112 maintains a substantially constant height, even though the cantilevers 113 may deflect and have variable height above the underlying fixed portion 108. As compared to an embodiment designed to allow the entire bottom surface of the deflectable portion 110 to flex, the disclosed configuration provides a more stable "inner point," and enables better correlation between measured cantilever movements and the corresponding applied forces.

The sensor device preferably omits any filler material disposed between the fixed portion 108 and the cantilevers 113. This allows regular deflection of the cantilevers 113 relative to the fixed portion 108 without obstruction or interference by other materials. For example, rubber or some other material may be used as a filler within the intervening space but is not preferred because it introduces additional complications (e.g., hysteresis, material properties of the filler material) in correlating measured cantilever deflection to actual applied forces.

The fixed portion 108 may also include one or more support brackets 106. In the illustrated embodiment, a pair of support brackets 106 are provided on opposite sides of the device. Each support bracket 106 houses a portion of a respective cantilever 113 and functions to limit the range of motion of the cantilever 113. For example, an outer portion of a cantilever 113 (and optionally a corresponding, coincident portion of the adaptor section 102) may pass through a bracket aperture 118 of the support bracket 106.

The aperture 118 is sized to limit the upward/downward movement of the cantilever 113. That is, as the outward portion of the cantilever 113 moves upward, the upper bound of the aperture 118 will eventually prevent further upward movement of the cantilever 113. Likewise, as the outward portion of the cantilever 113 moves downward (toward the fixed portion 108), the lower bound of the aperture 118 will eventually prevent further downward movement of the cantilever 113. The support brackets 106 may therefore function to limit deformation of the cantilevers 113 to levels within safe margins of deformation and to thereby prevent damage to the device caused by excessive and/or repeated applied torque.

The support brackets 106 may be attached to the base section 104 by way of connection apertures 120 and/or through other suitable fastening means. Though forming the support brackets 106 to be attachable/detachable from the other components is presently preferred, in other embodiments one or more support brackets may be integrally formed with the base section 104. Likewise, although the adaptor section 102 is shown here as separately formed and selectively attachable/detachable from the base section 104, some embodiments may include an adaptor section that is integrally formed with the base section 104. Because the support brackets 106 are fixed relative to the fixed portion 108, they may be referred to herein as a subcomponent of the fixed portion 108.

In the illustrated embodiment, each of the cantilevers 113 includes a holding aperture 114 disposed near the outer edge of the cantilever 113. Each of the support brackets 106 also include a holding aperture 116. The holding apertures 114 and 116 are configured to respectively hold magnets and corresponding Hall effect sensors (referred to hereafter as "Hall sensors" for convenience). Although the following description will refer to the holding apertures 114 as including magnets and the apertures 116 as including Hall sensors, it will be understood that in other embodiments these relative positions may be reversed. Also, although the illustrated embodiment utilizes Hall sensors and magnets to measure relative displacement of the cantilevers 113, other embodiments may additionally or alternatively include one or more other types of displacement sensors. For example, a resistive potentiometer may be utilized to measure displacement with one terminal located on the cantilever 113 and another terminal located on a corresponding portion of the fixed portion 108. In another example, a capacitive displacement sensor may be utilized with the sensor located on the fixed portion 108 and a suitable conductive target located on the cantilever 113, or vice versa. In another example, an optical sensor may be utilized by locating the sensor on the fixed portion 108 or cantilever 113 and configuring the sensor to measure relative displacement of the opposing component.

As used herein, the apertures 114 may be referred to as the "deflecting apertures" because they are located on the deflectable portion of the device while the apertures 116 may be referred to as the "fixed apertures" because they are located on a structure that is fixed relative to the deflectable portion 110 and its cantilevers 113. That is, the apertures 116 may be located in the support brackets 106, such as in the illustrated embodiment, and/or in other locations of the fixed portion 108.

In use, the cantilevers 113 deflect in response to applied axial and/or torsional forces, which causes the magnets in the apertures 114 to move relative to the Hall sensors in the apertures 116. The Hall sensors provide a voltage signal proportional in strength to the magnetic field at the Hall sensor. Because the strength of the magnetic field at the location of each Hall sensor will depend on the distance of the corresponding magnet relative to the Hall sensor, the voltage signals generated by the Hall sensors may be used to measure the applied axial and torsional forces.

The magnets and Hall sensors may be of any configuration suitable for providing sufficiently responsive readings within the given dimensions and operational conditions of the sensor device. For example, in one embodiment the magnets are 103 mg5 rare earth magnets available from Honeywell, and the Hall sensors are X98834-SS sensors as available from Honeywell.

Given the particular properties of the cantilevers 113 (e.g., dimensions, modulus of elasticity), the expected deflection of the cantilevers 113 upon exposure to a particular axial and/or torsional force can be readily determined, such as through straightforward empirical testing and/or through mathematical modeling methods (e.g., finite element analysis) known in the art. These deflections and the corresponding axial and/or torque forces involved may then be correlated to the voltage signals of the Hall sensors.

The components of the sensor device 100, including in particular the deflectable portion 110, are preferably formed to provide adequate elastic deformation in response to typical loads of a prosthetic device within the preferred size ranges of the device without risking breakage or plastic deformation. For example, typical loads involve forces of about 1,000 N and torques of about 60 Nm or up to about 120 Nm (e.g., about 120 Nm at the ankle during walking, 50 Nm at the knee during walking, and 110 Nm at the knee while climbing stairs). The material(s) used is preferably also be non-ferrous so as to avoid interfering with the magnetic field measurements of the Hall sensors. Titanium, such as Grade 5 Titanium, has proven effective in this regard, though other materials such as certain types of steel alloys and/or aluminum may also be suitable depending on particular cantilever geometry and application needs.

Although the illustrated embodiment places the fixed apertures 116 in the support brackets 106, other embodiments may include fixed apertures positioned at one or more other relatively fixed portions of the device. For example, optional fixed apertures 117 may be located directly in the fixed portion 108 at a location sufficiently close to the deflecting apertures 114 to allow for detection of changes in the magnetic field.

In addition, although presently preferred embodiments position the magnets in the deflecting apertures 114 and the Hall sensors in the fixed apertures 116 (and/or the fixed apertures 117), other embodiments may swap the relative positions of the magnets and Hall sensors. For example, Hall sensors may be placed in the deflecting apertures 114 while magnets are positioned in the fixed apertures 116 and/or 117. So long as one set of apertures is deflectable relative to another set, it is possible to detect changes in magnetic field strength and thus the degree of structural deflection and the force and/or torque associated with the deflection. In some embodiments, Hall sensors may be positioned on a circuit board, and the circuit board may be appropriately positioned and attached to the fixed portion 108. Such a circuit board may additionally include a battery, transmitter, signal filtering components, and/or other electronic components.

Figure 5:
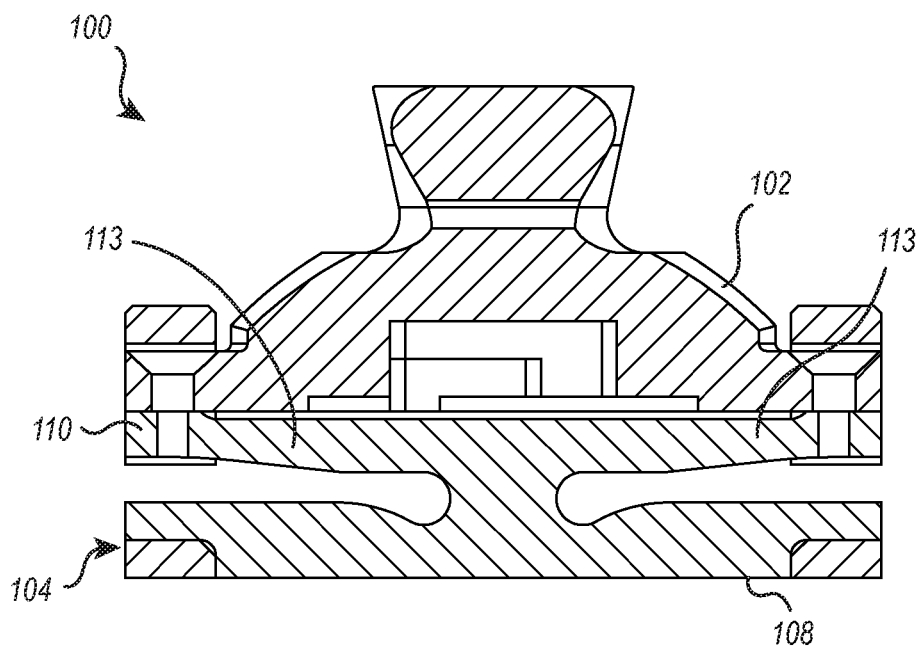
FIG. 5 is a schematic of the sensor device showing deflection of a deflectable portion during an axial load.
Figure 6:
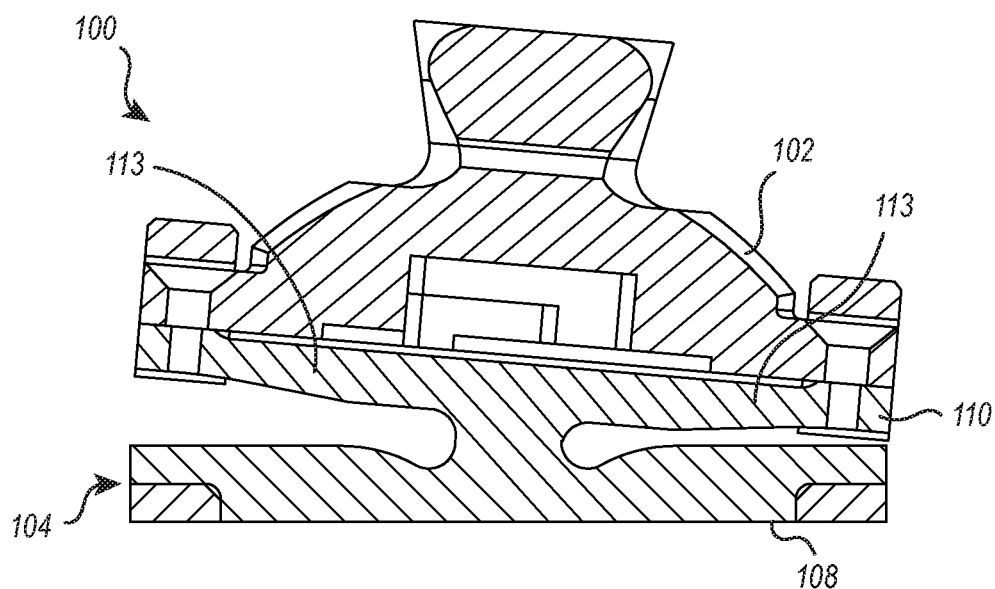
FIG. 6 is a schematic of the sensor device showing deflection of the deflectable portion during a torsional load.

FIG. 5 schematically illustrates deflection of the deflectable portion 110 during an axial load, and FIG. 6 schematically illustrates deflection of the deflectable portion 110 during a torsional load. Such axial and/or torsional forces may be transferred from the adaptor section 102 to the deflectable portion 110, causing an elastic deformation of its structure. This elastic deformation creates a displacement (e.g., millimeter-scale displacement) at the two outer ends of the cantilevers 113. In the case of a purely axial load as shown in FIG. 5, the cantilever ends each move in the same direction closer to the fixed portion 108. In the case of a torsional load as shown in FIG. 6, the opposing ends move in opposite directions with one moving closer to the fixed portion 108 and one moving further away from the fixed portion 108.

Upon displacement caused by axial and/or torsional loads, magnets (e.g., disposed at the cantilever ends) are moved relative to Hall sensors (e.g., disposed in fixed support brackets 106 or in other areas of the fixed portion 108), which changes the strength of the magnetic field as measured at the Hall sensors. The voltage outputs of the Hall sensors change accordingly and can then be used to measure the applied axial force and/or torque.

The sensor device may include a memory storage device and a suitable power source (e.g., battery) for storing force and/or torque readings. The stored data may be retrieved through a wired connection to the sensor device. Additionally, or alternatively, the sensor device may include a wireless transmitter capable of transmitting or otherwise communicating collected data via Wi-Fi, ultrahigh frequency radio wave connection (e.g., Bluetooth®), or other suitable wireless connection.

The sensor device is preferably configured to have dimensions and weight similar to those of a standard adaptor. This allows the sensor device to be easily integrated with a prosthetic without disrupting the weight or size of the prosthetic. For example, too much weight in the prosthetic can harm gait symmetry and introduce undesirable imbalances into the user's movement profile. In addition, maintaining a sensor device weight that is similar to a standard adaptor will allow users to have an experience similar to what they are accustomed to. The sensor device preferably weighs about 120 g or less, or about 100 g or less, or about 80 g or less, more preferably about 60 g or less, or even more preferably about 50 g or less. For example, the sensor device may weigh about 40 to 120 g, about 40 to 100 g, about 40 to 80 g, or about 40 to 60 g.

The size of the device is preferably similar to those of a standard adaptor. For example, the length may be about 50 mm (e.g., 35 to 65 mm), the width may be about 50 mm (e.g., 35 to 65 mm), and the height may be about 22 mm (e.g., 15 to 35 mm). Though device height can be compensated for by adjusting other portions of the prosthetic, such as pylon tubing, to be shorter, it is still preferable to keep the height within the foregoing dimensional range to maximize interchangeability and to reduce the need for custom adaptations for the sensor device.

The relatively small size and low weight of the sensor device are made possible because of the described sensing system based on magnets and Hall sensors. In contrast, a sensor device based on load cells will typically require larger-sized devices and/or devices with a greater weight. The relatively small size and low weight of sensor devices described herein allows for more straightforward and less problematic integration with prosthetic devices. For example, as compared to a load cell-based sensor, a sensor device as described herein may reduce issues related to excessive prosthetic weight, reduce the need for customized shortening of prosthetic components to make up for sensor size, and be readily installed in the same manner as a standard adaptor.

In addition, the sensor devices described herein may be operated without the need to amplify the generated signal. In contrast, a sensor that makes use of strain gauges to form a load cell must typically include additional signal amplification electronics built into the sensor to provide an adequate signal. This undesirably increases the size, complexity, and cost of the sensor.

It will be understood that although the illustrated embodiments are described in the context of use in a lower limb prosthesis, that sensor device embodiments may also be suitably used in other types of prostheses where force and/or torque sensing is desired. In addition, sensor device embodiments as described herein may be utilized in conjunction with non-prosthetic devices such as orthosis devices and other orthopedic devices (e.g., joint braces), exoskeleton devices, or robotic joints. Although these systems may not be used as prostheses in the technical sense, it will be recognized that their use involves similar challenges with respect to measuring applied forces and/or torque, and thus the principles and features described herein may be readily applied to such devices.

Some sensor devices may additionally include one or more inertial sensors as known in the art for measuring acceleration and/or velocity in addition to the axial and/or torsional forces measured by the device. Some embodiments that utilize Hall sensors may also include one or more reference Hall sensors in addition to the primary Hall sensors disposed closer to their respective corresponding magnets. For example, where the primary Hall sensors may be disposed closer to outer edges of the device, one or more reference Hall sensors may be positioned more inward radially (e.g., more inward by about 6 to 12 mm). Such reference Hall sensors beneficially compensate for stray magnetic fields, which are commonly seen in advanced prostheses due to the presence of electromechanical actuators.

The illustrated sensor device 100 includes a pair of cantilevers 113 positioned to provide torque measurement along a single plane. Typically, the sensor device 100 would be oriented so that the cantilevers 113 extend in the anterior and posterior direction, enabling measurement of torque in the sagittal plane, as these are the torque measurements usually of most interest to users and clinicians. The sensor device 100 may be alternatively oriented, however, according to other application needs or preferences. For example, the sensor device 100 may be oriented so that the cantilevers 113 extend in the medial and lateral directions, enabling measurement of torque in the frontal/coronal plane.

Figure 7:
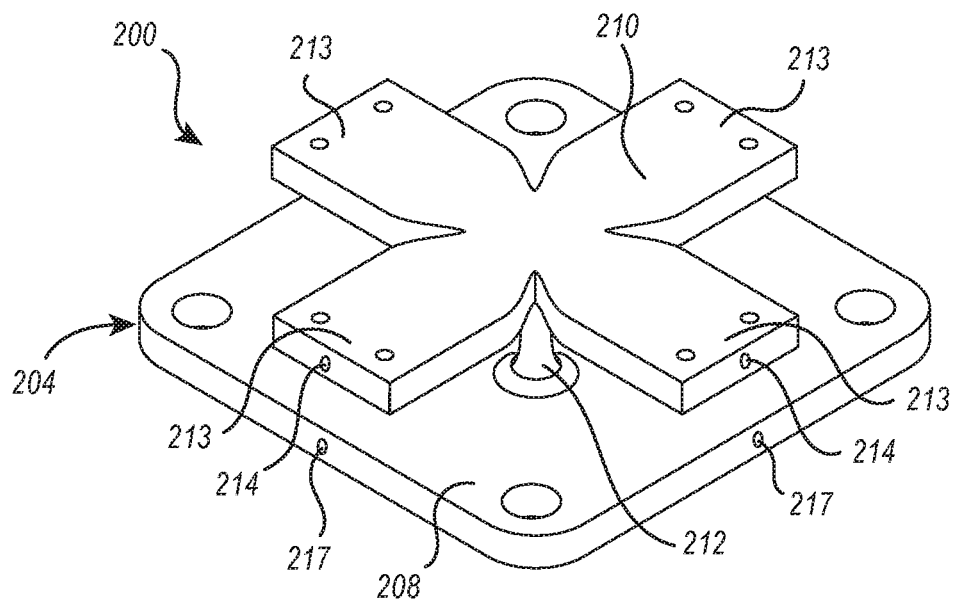
FIGS. 7 and 8 illustrates other embodiments of sensor devices each configured for measuring torque in more than one plane.

Alternative embodiments may include more than two cantilevers, or may include cantilevers of greater circumferential width, to enable measurement of torque in more than one plane. For example, FIG. 7 illustrates an embodiment of a base section 204 of a sensor device 200 where the deflectable portion 210 includes a set of four cantilevers 213 positioned to enable torque measurement in multiple planes. The sensor device 200 may otherwise be configured similar to the sensor device 100 described above and thus may include an adaptor section and/or support brackets (not shown). The deflecting apertures 214 are disposed near the edge of respective cantilevers 213 and correspond to fixed apertures 217 disposed in the fixed section 208 of the device (or to fixed apertures disposed in support brackets such as described above). As with the sensor device 100, magnets may be positioned within the deflecting apertures and Hall sensors may be positioned within the fixed apertures, or vice versa, to provide an output signal that corresponds to cantilever deflection and thus to the associated forces and torques acting on the cantilevers.

Embodiments having other numbers of cantilevers (e.g., 3, 6, 8, 12, etc.) are also possible. The number of cantilever elements included may depend on the desired granularity and detail of the measured force and torque readings. Typically, there will be an even number of cantilevers because each cantilever will usually be associated with an opposing cantilever extending in the opposite direction radially, though this need not be the case necessarily.

Figure 8:
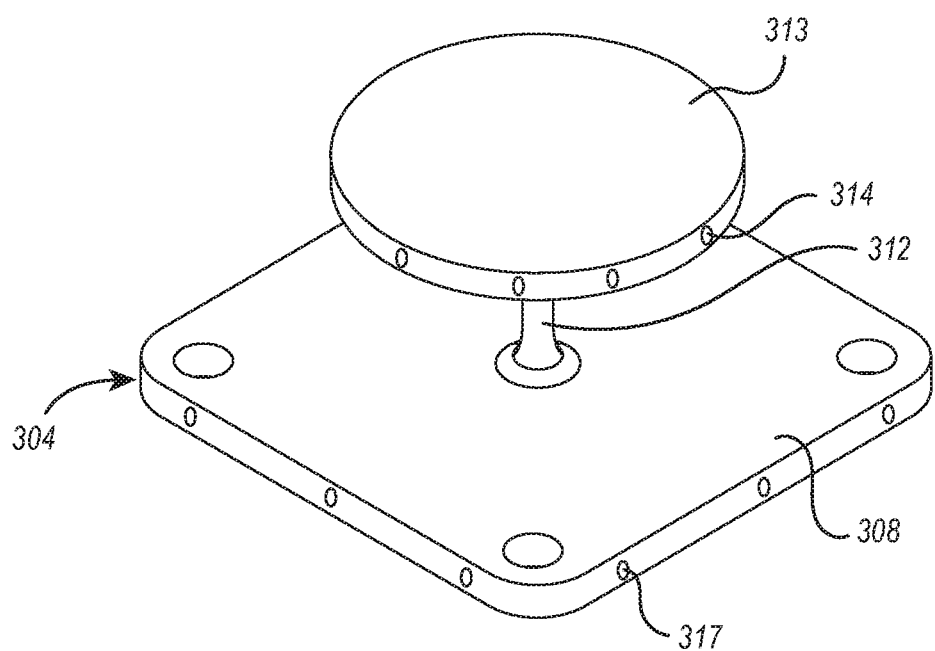

Other embodiments may include a deflectable section formed as plate or disk structure rather than independent cantilever elements. For example, as shown in FIG. 8, a base section 304 may include a plate/disk 313 attached to the pillar 312 so that the plate/disk is deflectable relative to the fixed portion 308 in a manner similar to the deflection of cantilever elements. The device includes attachment points (e.g., deflecting apertures 314 and fixed apertures 317) so that sensing components (e.g., magnets) are positioned near the outer edge of the deflectable plate/disk while corresponding sensing components (e.g., Hall sensors) are positioned in the fixed portion, or vice versa. A plate/disk embodiment may include multiple sensing components arranged around the circumference of the plate/disk (e.g., every 30 to 60 degrees, or other arrangement depending on desired measurement granularity), with corresponding sensing components likewise positioned in the fixed portion. The base section 304 may also include one or more support brackets (not shown) that may include apertures or other attachment points for sensing components. Such a support bracket can be configured in size and shape to fit over a at least a portion of the circumference of the plate/disk 313 to limit upward and/or downward deflection relative to the fixed portion 308.

The magnets and Hall sensors (collectively referred to as "sensing components") are described above as being insertable inside deflecting apertures or fixed apertures. This may be accomplished through a friction fit and/or with the assistance of an adhesive, for example. In some embodiments, one or more of the sensing components may be attached to or integrally formed with the associated device component rather than positioned within an aperture. For example, a magnet may be attached to the end section of a cantilever element using an adhesive, soldering, or other suitable attachment means, without necessarily first placing the magnet in an aperture. Likewise, a Hall sensor may be attached to a suitable fixed location without necessarily housing the Hall sensor within an aperture.

The terms "approximately," "about," and "substantially" as used herein represent an amount or condition close to the stated amount or condition that still performs a desired function or achieves a desired result. For example, the terms "approximately," "about," and "substantially" may refer to an amount or condition that deviates by less than 10%, or by less than 5%, or by less than 1%, or by less than 0.1%, or by less than 0.01% from a stated amount or condition.

It will be understood that elements described in relation to any embodiment depicted and/or described herein may be substituted for or combined with elements described in relation to any other embodiment depicted and/or described herein.

The invention claimed is:

1. A sensor device configured for measuring applied force and torque, the sensor device comprising:
   a base section, the base section including
      a deflectable portion having an inner point and one or more cantilevers extending outward in a coplanar fashion from the inner point,
      a fixed portion spaced apart from the deflectable portion such that the one or more cantilevers of the deflectable portion are deflectable relative to the fixed portion, the fixed portion including at least one support bracket extending from or attached directly to the fixed portion, the support bracket comprising an aperture configured to receive an outer portion of a corresponding cantilever and to limit deflection of the corresponding cantilever in response to a torsional force imparted to the corresponding cantilever by movement of a user, and
      a pillar extending between the inner point of the deflectable portion and the fixed portion to mechanically couple the deflectable portion to the fixed portion; and
   a plurality of sensing components configured to measure deflection of the one or more cantilevers relative to the fixed portion.

2. The sensor device of claim 1, wherein the plurality of sensing components are selected from the group consisting of Hall effect sensors and magnets, resistive potentiometers, capacitive displacement sensors, and optical sensors.

3. The sensor device of claim 1, wherein the plurality of sensing components comprise:
   at least one magnet, and
   at least one corresponding Hall effect sensor corresponding to the magnet and configured to measure magnetic field strength resulting from a distance between the Hall effect sensor and the corresponding magnet,
   wherein the sensing components are arranged such that output from the at least one Hall effect sensor relates to deflection of the one or more cantilevers relative to the fixed portion.

4. The sensor device of claim 3, wherein the magnet is attached at an outer edge of a corresponding cantilever, and wherein the Hall effect sensor is attached on the fixed portion of the base section.

5. The sensor device of claim 3, wherein the Hall effect sensor is disposed at the same radial distance as the magnet from the center of the sensor.

6. The sensor device of claim 1, further comprising an adaptor section having a bottom surface and a connection element extending away from the bottom surface, wherein at least outer edges of the one or more cantilevers are in mechanical contact with the bottom surface of the adaptor section.

7. The sensor device of claim 6, wherein the connection element is a male pyramid adaptor.

8. The sensor device of claim 1, wherein the support bracket includes an attachment point for a sensing component.

9. The sensor device of claim 1, further comprising an adaptor section having a bottom surface and a connection element extending away from the bottom surface, wherein at least outer edges of the one or more cantilevers are in mechanical contact with the bottom surface of the adaptor section, wherein a portion of the adaptor section also passes into the bracket aperture.

10. The sensor device of claim 1, wherein the deflectable portion has two cantilevers extending in opposite directions from one another from the inner point.

11. The sensor device of claim 10, wherein the fixed portion has two support brackets each associated with one of the two cantilevers and each being configured to limit deflection of the respective cantilever.

12. The sensor device of claim 11, wherein a Hall effect sensor is attached to each support bracket and wherein a magnet is attached to an outer edge of each cantilever.

13. The sensor device of claim 1, wherein the base section further includes at least one fastening structure for fastening the sensor device to a prosthesis component.

14. A prosthetic device, comprising:
   first and second prosthetic components; and
   a sensor device as in claim 1 disposed between and attached to the first and second prosthetic components.

15. The prosthetic device of claim 14, wherein the prosthetic device is a lower limb prosthetic.

16. The prosthetic device of claim 15, wherein the sensor device is disposed at an ankle joint.

17. The prosthetic device of claim 15, wherein the sensor device is disposed at a knee joint.

18. A powered exoskeleton device comprising a sensor device as in claim 1.

19. The sensor device of claim 1, wherein the plurality of sensing components comprise a primary Hall effect sensor and a reference Hall effect sensor disposed radially inward with respect to the primary Hall effect sensor.

20. A sensor device configured for measuring applied force and torque, the sensor device comprising:
- a base section, the base section including
  - a deflectable portion having an inner point and one or more cantilevers extending outward in a coplanar fashion from the inner point,
  - a fixed portion spaced apart from the deflectable portion such that the one or more cantilevers of the deflectable portion are deflectable relative to the fixed portion, wherein the fixed portion further includes at least one support bracket extending from or attached directly to the fixed portion, the support bracket comprising an aperture configured to receive an outer portion of a corresponding cantilever and to limit deflection of the corresponding cantilever in response to a torsional force imparted to the corresponding cantilever by movement of a user, and
  - a pillar extending between the inner point of the deflectable portion and the fixed portion to mechanically couple the deflectable portion to the fixed portion; and
- a plurality of sensing components configured to measure deflection of the one or more cantilevers relative to the fixed portion, wherein the plurality of sensing components includes at least one magnet and at least one corresponding Hall effect sensor corresponding to the magnet and configured to measure magnetic field strength resulting from a distance between the Hall effect sensor and the corresponding magnet,
- wherein the sensing components are arranged such that output from the at least one Hall effect sensor relates to deflection of the one or more cantilevers relative to the fixed portion.

* * * * *